March 4, 1941. B. RUYS Plant Pat. 460
BARBERRY PLANT
Filed March 5, 1940
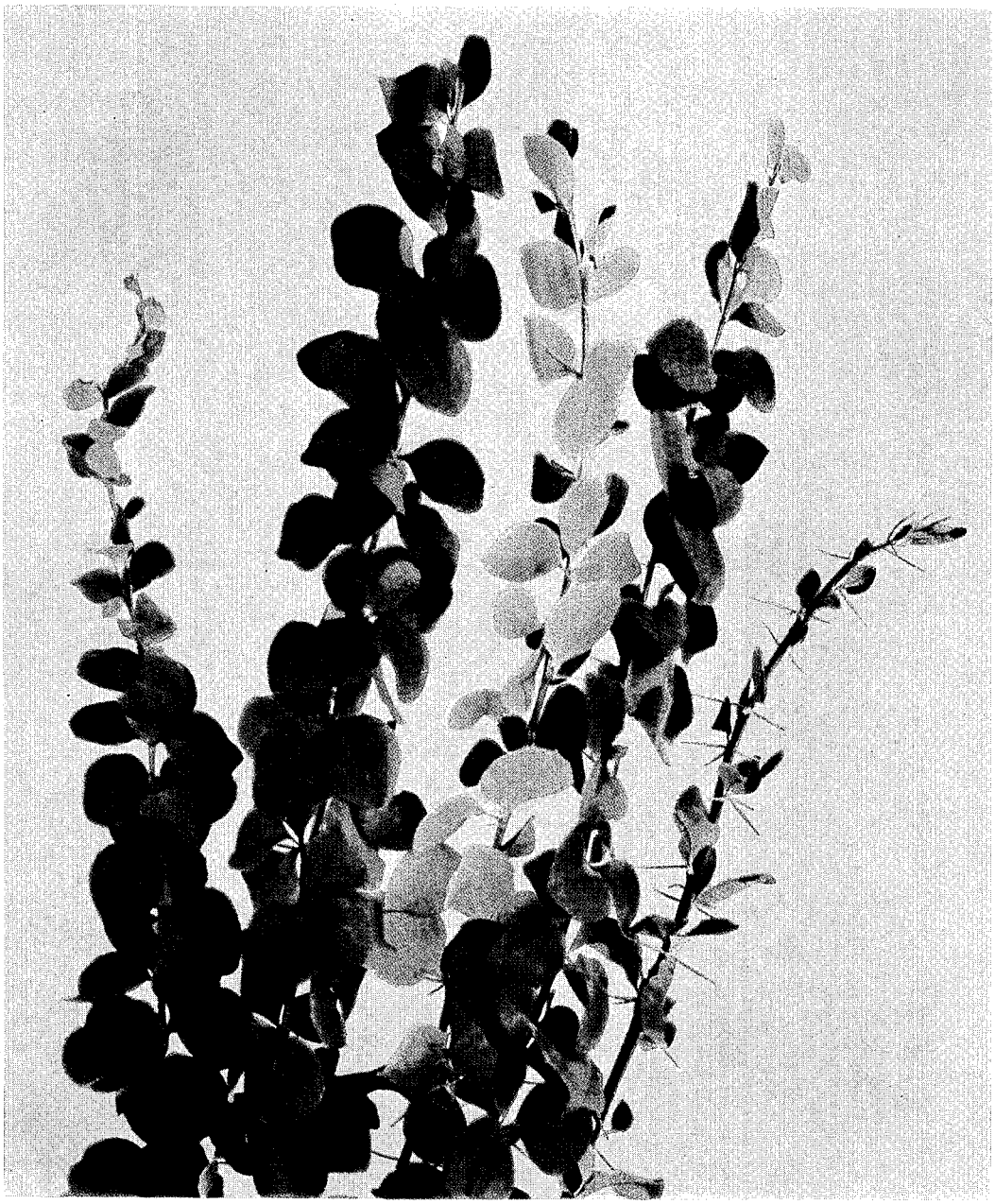
Inventor:-
Bonne Ruys
By: Cobb & Cobb
Attorneys Patented Mar. 4, 1941

Plant Pat. 460

UNITED STATES PATENT OFFICE

460

BARBERRY PLANT

Bonne Ruys, Dedemsvaart, Netherlands, assignor to E. D. Smith & Sons, Limited, Winona, Ontario, Canada Application March 5, 1940, Serial No. 322,410

1 Claim. (Cl. 47—59)

My invention relates to a new and distinct variety of barberry which originated as a chance seedling. The new variety discovered by me is endowed with definitely new and unusual characteristics which distinguish it from the well known *Berberis Thunbergii* var. *atropurpurea* and other varieties. I have determined by asexual reproduction of the new variety that these new characteristics are permanently fixed.

My new variety is fully as hardy as *B. Thunbergii atropurpurea*. However, the chief advantages over *B. Thunbergii atropurpurea* reside in the much stronger and coarser growth and the more spreading habit of growth of the new variety, thereby affording a more robust type of plant. These advantages are emphasized by the unusually large size of the leaves as compared with those of the common *Berberis Thunbergii atropurpurea*. The color of the leaves of my new variety is a further important feature of novelty, especially in combination with the robust habit of growth, whereby a more colorful and attractive appearance is presented as compared with the common *atropurpurea*. From a commercial point of view, this greatly enhances the value of the new variety. The novel color of the leaves above referred to may be generally described as a deep, soft purple above, and a silvery purple beneath.

The prominent distinctions and characteristics of my new variety will become fully apparent by reference to the following detail description and to the accompanying drawing, the latter showing typical specimen branches of a three year old plant grown in the Province of Ontario, Canada.

In the description of my new variety as given below, the color designations are in accord with Ridgway's Color Standard as regards the description of the color of the stems, leaves and thorns. Other references to color are given in accordance with ordinary dictionary terms.

*Description*

Habit of growth: As previously mentioned, the plant is a strong grower, attaining an average height of 2.5 meters, and develops many branches with strongly grooved branchlets.

The habit of growth is spreading with long, gracefully arching branches on the older plants, in contrast to the erect, bunchy, dense growth of the parent.

Young shoots:

*Stems.—Color*—Bordeaux, Plate XII.
Amaranth Purple, Plate XII.

Mature shoots:

*Stems.—Color*—Burnt Lake, Plate XII.

Thorns:

*Borne.*—In triplets, of fan shape on mature stems, 15–20 mm. long.

*Color.*—Deep Chrysolite Green, Plate XXXI.

Foliage:

*Arrangement.*—Very unequal.

The individual leaves are larger and distinct in shape, being cordate and somewhat crenate, whereas that of the parent are spatulate and entire;

*Form.*—1–5 cm. long, obtuse, rarely acute, narrowed at base into a petiole 2–5 mm. long, with mid-rib generally protruding beyond margin of the leaf and terminating in a minute prickle.

*Color of young leaves.—Face*—tones of Indian Purple, Plate XXXVIII, Dk. Corinthian Red, Plate XXXVIIII, Indian Red, Plate XXVII, blending to Brownish Olive, Plate XXX, at base of leaf. *Back*—light Vinaceous Lilac, Plate XLIV, with veins of Dull Indian Purple, Plate XLIV.

*Color of Mature Leaves.—Face*—tones of Dk. Purple-drab, Plate XLV, Taupe Brown, Plate XLIV, Dk. Livid Brown, Plate XXXIX, Dk. Vinaceous Brown, Plate XXXIX, Dk. Corinthian Purple, Plate XXXVIII, Mineral Red, Plate XXVII, blending to Dk. Ivory Green, Plate XLVII, Andover Green, Plate XLVII, Deep Grape Green, Plate XLI. *Back*—Pale Vinaceous Drab, Plate XLV.

(Leaves redden towards tips of branches; greener towards base of branches.)

By way of comparison, the color of the foliage may be said to be dark as compared to the more shiny and red purple color leaves of *Berberis Thunbergii atropurpurea*.

Flowers:

*Borne.*—Solitary or 2 to 5 and fasicled or umbellate and peduncled.

*Size.*—8–10 mm. across.

*Color.*—Yellow, reddish outside.

*Pedicels.*—6–10 mm. long.

Fruit:

*Form.*—Ellipsoid.

*Size.*—7–8 mm. long.

*Color.*—Purplish Red.

I claim:

A new and distinct variety of barberry characterized particularly by its coarse, free branching, spreading, and robust habit of growth, the shape and size of its leaves and their attractive color, and by its hardness, substantially as shown and described.

BONNE RUYS.